United States Patent [19]
Österdahl et al.

[11] Patent Number: 6,080,909
[45] Date of Patent: *Jun. 27, 2000

[54] ABSORBENT BODY AND APPARATUS FOR ITS MANUFACTURE

[75] Inventors: Eje Österdahl, Västra Frölunda; Ted Guidotti, Göteborg, both of Sweden

[73] Assignee: SCA Hygiene Products AB, Goteborg, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/696,946
[22] PCT Filed: Feb. 22, 1995
[86] PCT No.: PCT/SE95/00185
§ 371 Date: Aug. 22, 1996
§ 102(e) Date: Aug. 22, 1996
[87] PCT Pub. No.: WO95/22952
PCT Pub. Date: Aug. 31, 1995

[30] Foreign Application Priority Data

Feb. 24, 1994 [SE] Sweden ................................. 9400642

[51] Int. Cl.[7] .................................................. A61F 13/15
[52] U.S. Cl. ........................ 604/368; 604/378; 264/257
[58] Field of Search ..................... 604/380, 368, 604/378, 385.1; 264/280, 294, 257–260, 261

[56] References Cited

U.S. PATENT DOCUMENTS

| | | |
|---|---|---|
| 4,027,672 | 6/1977 | Karami ..................... 604/380 |
| 4,232,674 | 11/1980 | Melican . |
| 4,360,021 | 11/1982 | Stima ........................ 604/368 |
| 4,592,751 | 6/1986 | Gegelys .................... 604/368 |
| 4,596,567 | 6/1986 | Iskra ......................... 604/368 |
| 4,662,876 | 5/1987 | Wiegner .................... 604/368 |
| 4,892,535 | 1/1990 | Bjornberg et al. ....... 604/380 |
| 4,994,053 | 2/1991 | Lang . |
| 5,118,376 | 6/1992 | Pigneul et al. . |
| 5,134,007 | 7/1992 | Reising et al. ........... 604/378 |
| 5,139,841 | 8/1992 | Makoui et al. .......... 604/378 |
| 5,141,794 | 8/1992 | Arroyo ..................... 604/378 |
| 5,175,046 | 12/1992 | Nguyen . |
| 5,242,435 | 9/1993 | Murji et al. .............. 604/378 |
| 5,356,405 | 10/1994 | Thompson et al. ...... 604/378 |
| 5,547,747 | 8/1996 | Trokhan et al. ......... 604/380 |
| 5,601,542 | 2/1997 | Melius et al. ............ 604/368 |

FOREIGN PATENT DOCUMENTS

| | | |
|---|---|---|
| 0 160 572 | 11/1985 | European Pat. Off. . |
| 1 566 594 | 5/1980 | United Kingdom . |
| 2 132 897 | 7/1984 | United Kingdom . |
| WO 80/01455 | 7/1980 | WIPO . |
| WO 92/19198 | 11/1992 | WIPO . |

*Primary Examiner*—John G. Weiss
*Assistant Examiner*—Dennis Ruhl
*Attorney, Agent, or Firm*—Burns, Doane, Swecker & Mathis, L.L.P.

[57] ABSTRACT

An absorbent body and an apparatus for manufacturing an absorbant body having at least two layers of absorbent material, upon each of which a layer of superabsorbent particles has been laid. The particle layers include patterns of through-penetrating openings and one of the particle layers is horizontally displaced in relation to another of the particle layers.

26 Claims, 5 Drawing Sheets

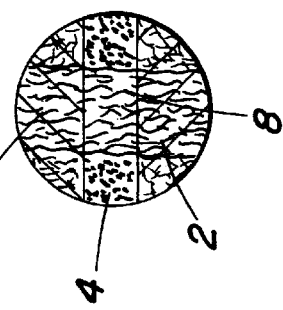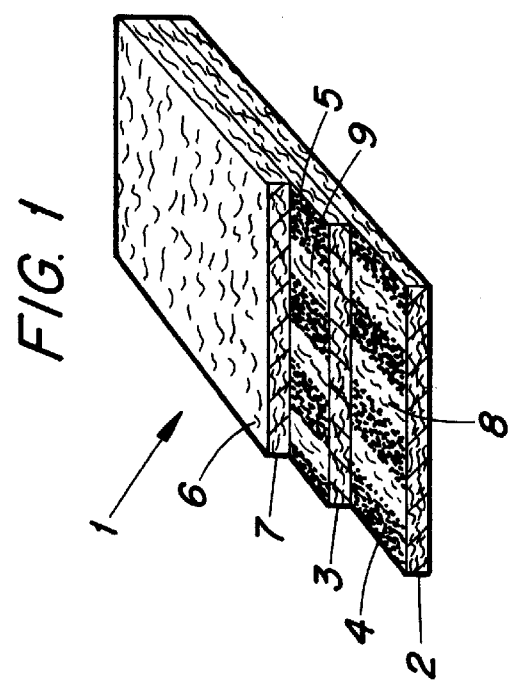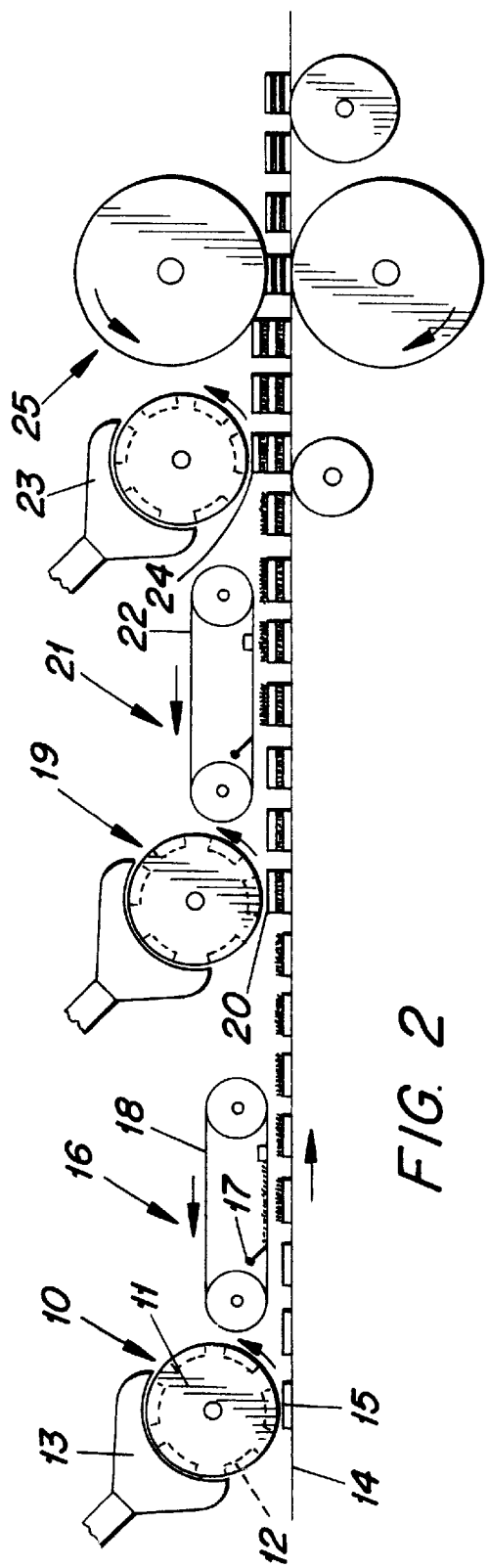

ABSORBENT BODY AND APPARATUS FOR ITS MANUFACTURE

BACKGROUND OF THE INVENTION

1. Field of the Invention

The present invention relates to an absorbent body for an absorbent article, such as a diaper, an incontinence guard or a sanitary napkin, comprising a sheet or layer of absorbent material and a layer of particles of so-called superabsorbent material placed on the sheet of absorbent material. The invention also relates to an arrangement of apparatus for producing such an absorbent body.

2. Description of Related Art

The absorption capacity of present-day absorbent bodies in absorbent articles of the aforementioned kind is generally sufficient to be able to absorb all liquid discharged by the wearer over a normal period of use. Leakage problems associated with articles of this kind are more often than not contingent on the ability of the absorbent body to utilize its intrinsic absorption capacity to a sufficiently great extent. Decisive factors in this regard are the ability of the article to disperse and to receive liquid, i.e. on the effectiveness of its liquid transport properties. By liquid-receiving properties is meant in the present document the ability of the absorbent body to takeup a given quantity of discharged liquid quickly, i.e. its ability to transport liquid from the surface of the body into the interior thereof. The higher the liquid-receiving capacity, the quicker the discharged liquid is transported into the absorbent body.

At present, it is conventional to provide the absorbent bodies of such absorbent articles with so-called superabsorbent material, with the intention of increasing the total absorption capacity of such bodies. By superabsorbent material is meant material which is able to absorb liquid in quantities that correspond to many times the weight of the material. Such material is often used in the form of powder, grains, granules, flakes, short fibres or similar particle forms. In the case of materials of this kind, the liquid absorbed forms a gel. The materials also have low liquid-dispersing ability. Consequently, in order to utilize the high absorption capacity of superabsorbent materials, it is necessary to arrange the materials so that discharged liquid can be transported to all parts of the superabsorbent material.

This can be achieved by mixing particles of superabsorbent material in a layer of heavily compressed cellulose fluff pulp, wherewith the capillary forces in the fluff pulp layer spread the liquid throughout the layer and therewith to the superabsorbent particles mixed therein.

It is also known to use separate layers of superabsorbent material which coact with spreading or dispersion layers disposed on one side or on both sides of the layer of superabsorbent material. One problem that arises when using separate layers of superabsorbent material is so-called gel blocking, i.e. the gel that is formed when the superabsorbents absorb liquid prevents liquid from flowing through the layer.

U.S. Pat. No. 4,994,053 teaches an absorbent article in which a sheet or layer which includes a pattern of discrete regions containing superabsorbent particles drains an overlying cellulose fluff layer, while U.S. Pat. No. 5,118,376 teaches an absorbent article in which superabsorbent particles are contained in a pattern of hollows or pits in a fibre mat, this pattern being produced by mechanical compression of the fibre mat in said pitted regions with the aid of an embossing cylinder or roller.

Absorbent bodies in which particles of superabsorbent material are mixed into a layer of cellulose fluff pulp normally have better liquid-receiving properties than absorbent bodies in which fluff pulp and particles are applied in mutually separate layers, particularly after several liquid discharges. On the other hand, layered absorbent bodies normally have better rewetting properties, i.e. which when the article is subjected to load are better able to retain the liquid absorbed by the absorbent body than absorbent bodies in which the particles are mixed in the fluff pulp.

In the case of the absorbent articles before mentioned, the total liquid discharge is periodic, by which is meant that a given quantity of liquid is discharged almost instantaneously, whereafter a relatively long time will follow before the next discharge. In the case of diapers and incontinence guards, a large amount of liquid may be discharged on each occasion, which places high demands on the ability of the diaper to quickly transport the discharged liquid from the surface of the diaper and into the absorbent body, i.e. the body must possess good liquid-receiving properties in order to minimize the risk of leakage. Since liquid is discharged several times during the time in which an absorbent article of this kind is intended to be worn, it is desirable that the absorbent article will have good liquid-receiving properties on all those liquid discharges that occur during the intended use period of the article. Naturally, the liquid transport properties of the article are at their best before the first liquid discharge and are successively impaired with subsequent discharges, although it is important that this impairment is kept as low as possible.

SUMMARY OF THE INVENTION

An object of the present invention is to improve the liquid-receiving properties of a layered absorbent body while retaining its good rewetting properties.

In accordance with the invention, this object is achieved with an absorbent body of the kind defined in the introduction which is characterized in that the layer of particle material includes a pattern of through-penetrating openings. Such an arrangement greatly improves the liquid-receiving properties of the absorbent body in comparison with a corresponding absorbent body comprising a fully covering layer of particle material, while essentially retaining the good rewetting properties of the body at the same time.

According to one preferred embodiment of the invention, the absorbent material is comprised of a fibre structure and the particles in the particle layer are enclosed either completely or partially in the fibre structure. The absorbent body also includes several layers of absorbent material on which layers of particles are placed, these layers including patterns of through-penetrating openings. The openings in the different particle layers are preferably offset horizontally in relation to one another and overlap each other. It has been surprisingly found that when the absorbent body is constructed in this way, the liquid-receiving properties are improved to such an extent as to correspond to the properties of absorbent bodies in which the particles are mixed in absorbent material, such as fluff pulp, without appreciably impairing the rewetting properties.

The layers of absorbent material are preferably comprised of compressed cellulose fluff pulp and the penetrating openings in the layer of particle material are filled with a cellulose fluff pulp that has been compressed to a lesser extent than the cellulose fluff pulp that is located externally of the openings in parts of the layer of cellulose fluff pulp lying beneath the layer of particle material. An advantage is afforded when the aforesaid layers are comprised of a fibre material which has a high liquid-dispersing ability, for instance chemithermomechanical fluff pulp, chemically stiffened cellulose fibres, synthetic wadding, etc., preferably arranged on top of the uppermost particle layer, i.e. outermost on that side of the absorbent body which when an absorbent article containing the absorbent body is worn lies nearest to the wearer's body, and particles of so-called superabsorbent material are admixed in the fibre material in the upper layer or sheet. According to one advantageous variant, the pattern of openings in each particle layer is comprised of discrete slots which extend in the longitudinal direction of the absorbent body along the whole of its length.

The invention also relates to an arrangement of apparatus for manufacturing absorbent bodies for such absorbent articles as diapers, incontinence guards or sanitary napkins, said apparatus being characterized by means for applying particles in a specific pattern on a moving web of material, means for moving a first fibre body past the particle applying means, means for laying a second fibre body on top of the first fibre body subsequent to having applied a layer of particles on said first fibre body, means for applying on the second fibre body a layer of particles in a specific pattern which is displaced in relation to the particle pattern formed on the first fibre body, and means for compressing the thus composed absorbent body. Respective means for applying particles on the first and the second fibre bodies will each preferably include a particle dispenser, a belt which runs above the fibre body concerned and which includes a pattern of holes corresponding to the applied particle pattern and which is spaced from the fibre body at least to an extent which will enable the particles laid on the fibre body to be accommodated between the belt and said body, wherein the particle dispenser is intended to dispense particles continuously in a uniform and broad stream whose width is equal to or slightly greater than the width of the hole pattern on the belt, and further comprises means for carrying away particles caught by the belt.

BRIEF DESCRIPTION OF THE DRAWINGS

The invention will now be described in more detail with reference to the accompanying drawings, in which FIG. 1 is a perspective, partly cut-away view of one embodiment of an inventive absorbent body;

FIG. 1a is a cross-sectional view of an enlarged section of the absorbent body shown in FIG. 1;

FIG. 2 is a schematic illustration of an arrangement for manufacturing the absorbent body shown in FIG. 1;

DETAILED DESCRIPTION OF THE INVENTION

Figure 3:
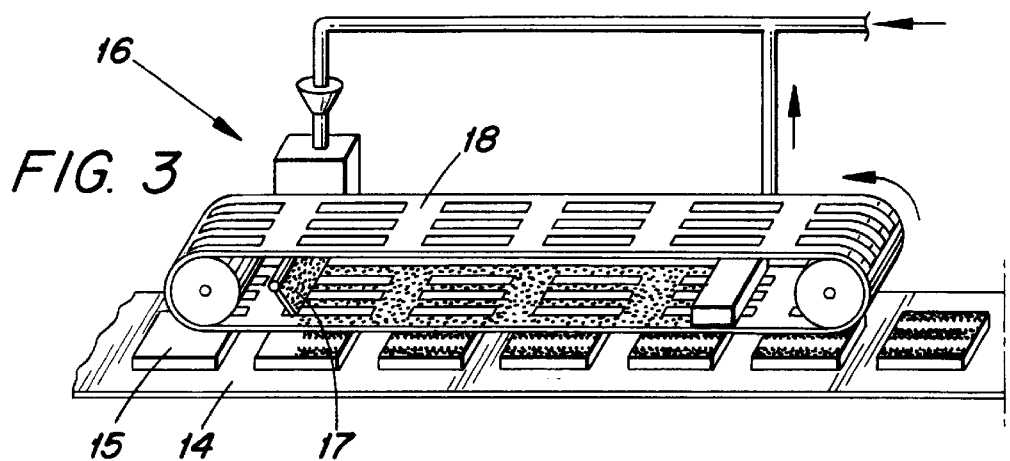
FIG. 3 illustrates a device for delivering particles to an underlying material web included in the arrangement shown in FIG. 2.
Figure 4A:
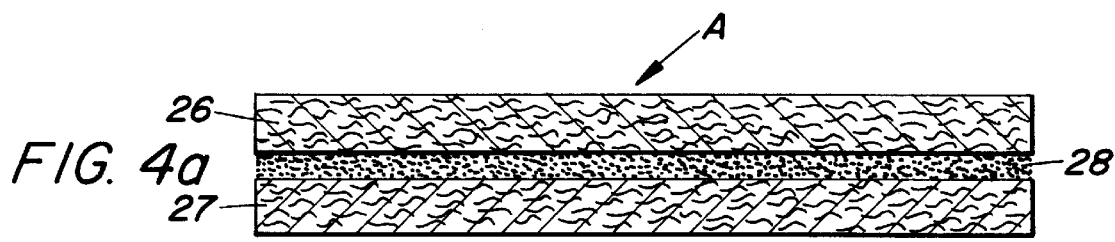
FIG. 4 illustrates schematically cross-sectional views of four different test bodies.
Figure 4B:
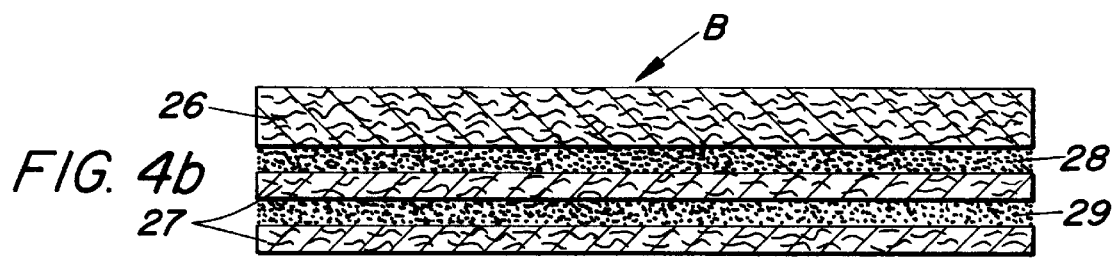
Figure 4C:
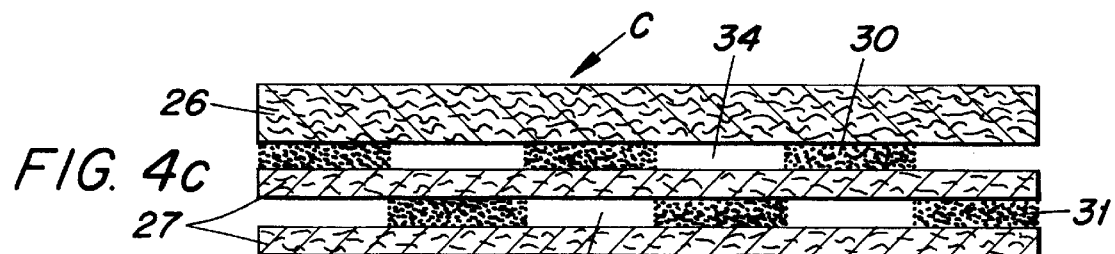
Figure 4D:
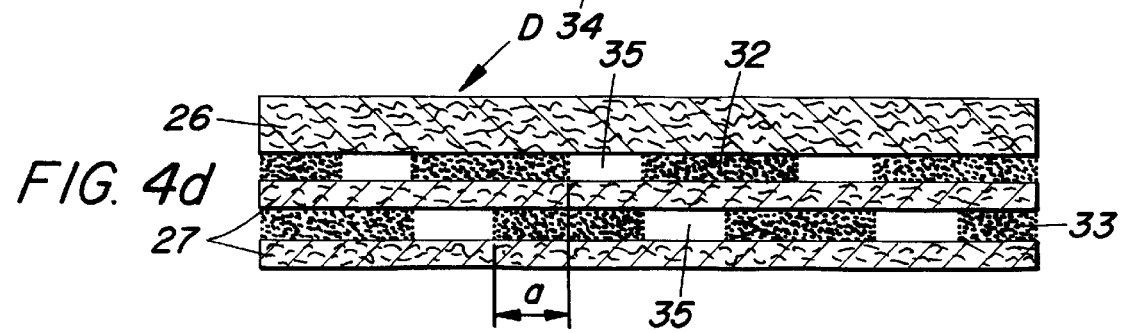

The absorbent body 1 illustrated in FIG. 1 includes two layers 2, 3 of a fibre structure having good liquid-dispersing or spreading properties, for instance two layers of chemical cellulose fluff pulp, on which layers 4, 5 of particles of so-called superabsorbent material are applied.

The absorbent body 1 also includes a layer or sheet 6 of a fibre structure having a high instantaneous liquid-receiving ability, for instance a layer of chemithermomechanical cellulose fluff pulp, chemically stiffened cellulose fibres, synthetic wadding or the like, in which particles 7 of superabsorbent material are mixed.

The layers 4, 5 of superabsorbent particles include respective openings 8 and 9 in the form of slots which extend in the longitudinal direction of the absorbent body 1, along the whole of its length. The openings 8, 9 in respective layers 4, 5 are displaced horizontally in relation to one another. The term vertical direction, or vertically, as used in the present document infers a direction which is at right angles to that side of the absorbent body which when using an absorbent article which includes an inventive absorbent body lies proximal to the wearer's body.

FIG. 2 illustrates schematically an arrangement for continuous manufacture of absorbent bodies 1. The arrangement includes a first conventional mat-forming wheel 10 which includes a rotary forming cylinder 11 provided with moulds 12 which are filled successively with air-transported cellulose fibres with the aid of an applied sub-pressure as the cylinder passes a header or hood 13 into which a fluff-pulp air-transport conduit dischargers. After the moulds 12 have passed the hood 13, the bodies 15 formed in the moulds are deposited onto an underlying moving conveyor belt 14 with the aid of an applied overpressure.

The deposited bodies 15 are then conveyed by the conveyor belt 14 beneath an applicator device 16 which deposits particles onto the bodies 15 in a specific pattern. The device 16 is illustrated in perspective in FIG. 3 and, in principle, is constructed in the same manner as the particle applicator illustrated and described in SE-B 468,305. The device thus includes a particle dispenser 17 which dispenses particles in a uniform and broad stream onto a belt 18 provided with a pattern of holes. As will be seen from FIG. 3, in the illustrated case the hole pattern on the belt 18 is comprised of a sequence of rows of slot-like openings formed in the belt and through which the particles dispensed by the particle dispenser or applicator fall down onto the passing bodies 15. As will be understood, the speeds at which the belt 18 and the conveyor belt 14 move are synchronized with one another so that spaces between the rows of slots on the belt 18 will coincide with spaces between the bodies 15 and so that the particles will be deposited along the full length of the bodies. The reader is referred to the aforesaid document for a more detailed explanation of the construction of the device 16.

After having passed the device 16, the shaped or moulded bodies 15 carrying a pattern of particles pass beneath another mat-forming wheel 19 at which a second moulded body 20 is placed on top of the layer of particles carried by the body 15, whereafter the thus formed three-tier body passes beneath a second particle applicator 21. The particle applicator 21 is similar to the particle applicator 16 with the exception that the slots in the belt 22 of the applicator 21 are displaced transversely to the direction of movement of the conveyor belt 14 in relation to the slots in the belt 18 of the applicator 16. The particle patterns on the bodies 15 and 20 will therefore be displaced transversely in relation to one another.

The composite body comprised of the moulded bodies 15, 20 and the particle layers carried thereby then passes beneath a third mat-forming wheel 23 where a third moulded body 24 is placed on top of each of the stack of bodies 15, 20 and the particle layers carried thereby. The composite body comprised of the aforesaid three moulded bodies and the two particle layers then passes through a pair of compression rollers 25. As the composite body is compressed, the particle layers are pushed into respective underlying bodies 15, 20 and the resultant slot-like openings thereby formed in the particle layers are filled with fluff pulp which has been compressed to a lesser degree than the fluff pulp in the moulded bodies by said compression. This phenomenon is illustrated schematically in FIG. 1a, which illustrates a section of the absorbent body shown in FIG. 1 containing the particle layer 4, the layers of fluff pulp 2, 3 and a slot-like opening 8.

With the intention of establishing the effects of the invention, there was carried out a first comparison test in which two mutually different test bodies constructed in accordance with the invention were compared with two different test bodies of a known kind with regard to the liquid-receiving and rewetting properties of the test bodies.

The four test bodies A–D are shown in FIG. 4, from which it will be seen that each body includes a top layer 26 comprised of chemithermomechanical cellulose fluff pulp with which particles of a superabsorbent material have been admixed. The superabsorbent material constitutes 10 percent by weight of the layer 26. Each of the test bodies A–D also includes a bottom layer 27 of chemical cellulose fluff pulp. The test body A has a layer 28 of superabsorbent particles sandwiched between the top and bottom layers 26 and 27. The test body B differs from the test body A by virtue of the fact that it comprises two fluff layers 27 and a layer 29 of superabsorbent particles between said layers. The test bodies C and D are constructed in the same manner as the test body B, except that the respective layers of superabsorbent particles 30, 31 and 32, 33 include a pattern of through-penetrating slots 34 and 35, these slots extending along the full length of respective bodies and being shown in the sectional views of FIG. 4. In test body C, the slots 34 in the different particle layers 30, 31 are displaced in relation to one another so as to be mutually separated horizontally, whereas the slots 35 in the particle layers 32, 33 of the test body D overlap one another horizontally. The open area in the particle layers 30, 31 of test body C is 50%, whereas the open area in the particle layers 32, 33 in test body D is 30%.

The test bodies were all of the same size, 100×280 mm, and were constructed from the same materials. The body A had a surface weight of 843 g/m² and a density of 166 g/dm³, the body B had a surface weight of 840 g/m² and a density of 164.8 g/dm³, the body C had a surface weight of 836 g/m² and a density of 169.5 g/dm³, and the body D had a surface weight of 861 g/m² and a density of 171.1 g/dm³. All test bodies contained the same amount of absorbent material.

The test bodies were tested in the following manner:

There was first applied 60 ml of test liquid (0.9% NaCl-solution) through a hole of 80 mm in diameter in a plate placed on the top layer 26. The admission time was measured, i.e. the time taken before all liquid had been absorbed by the test body. This procedure was repeated three times at 20-minute intervals between each liquid delivery. Rewetting was measured after the third liquid delivery, by placing eight filter papers on top of the test body and subjecting the papers to a load of 1.1 kg (2.8 kPa) for 15 seconds. The filter papers were weighed before and after applying the load and their increase in weight recorded. Liquid was then applied for a fourth time and the rewetting tendencies of the bodies was again measured.

Figure 5:
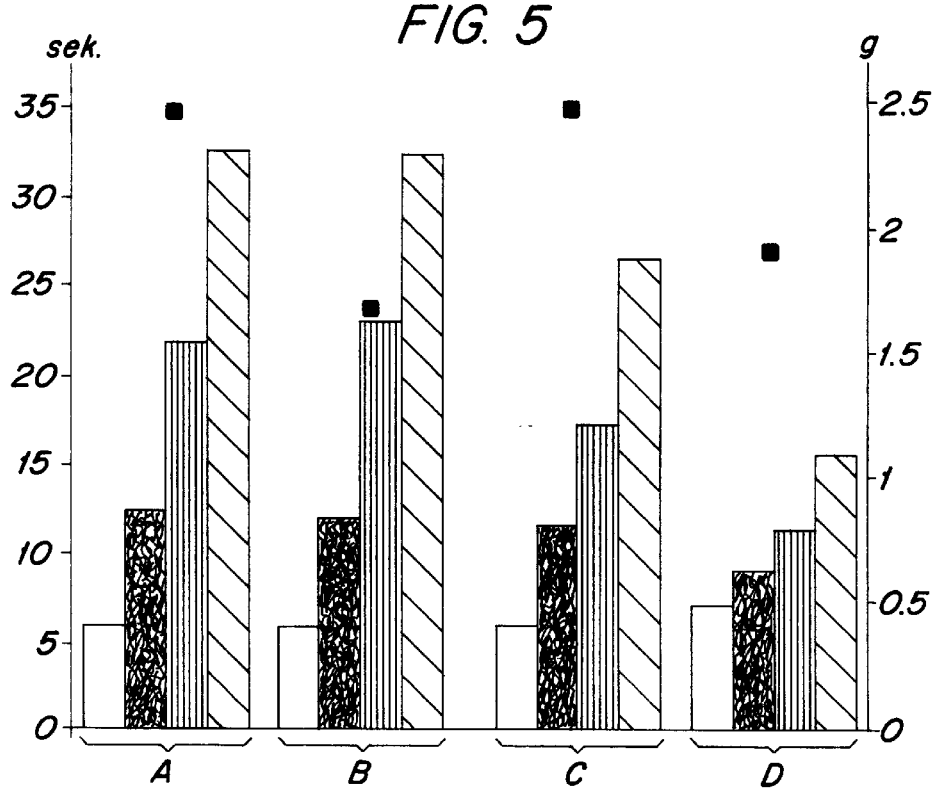
FIG. 5 is a bar chart illustrating the liquid-receiving time for the test bodies in FIG. 4 on four successive liquid discharge occasions and rewetting after the third liquid discharge occasion.

The results of this test are shown in FIG. 5, which is a stack chart showing the liquid-receiving properties of the test bodies A–D. Each liquid delivery is symbolized by a stack and the height of each stack illustrates the admission time in seconds and can be read-off from the scale shown to the left of the Figure. The four liquid deliveries are represented sequentially by an empty or hollow stack, a gray stack, a black stack and a hatched stack. The scale shown to the right of the Figure shows the weight in grams of the liquid that has been absorbed by the filter papers and constitutes a measurement of the rewetting properties. The measured increase in weight of the filter papers is symbolized in FIG. 5 by a solid square.

It will be seen from FIG. 5 that the liquid-receiving properties of test bodies A and B were essentially the same, whereas rewetting was less pronounced in the case of test body B. With regard to liquid transportation, it can be concluded from this that it is more beneficial to provide an absorbent body with two particle layers than with one layer, assuming, of course, that the layers 27 are constructed from material which has good liquid-dispersion ability.

It will also be seen from the comparison illustrated in FIG. 5 that the test bodies C and D have better liquid-receiving properties than the bodies A and B. It will also be seen that rewetting properties were good. Despite its large open area in the particle layers 30, 31, the body C had a rewetting tendency which corresponded to the rewetting tendency of the body A, while the rewetting tendency of the body D was only insignificantly greater than the rewetting tendency of the body B.

The test body D surprisingly exhibited good liquid-receiving properties which corresponded essentially with the liquid-receiving properties of absorbent bodies comprised of cellulose fluff pulp with uniformly intermixed particles of superabsorbent material. Because the test body D had a much smaller open area than the test body C, it could be expected that it would have poorer liquid-receiving properties than the body C and not better liquid-receiving properties, as was the actual case. It will also be seen from the stack chart in FIG. 5 that the admission time in the case of test body D was short even on the occasion of the fourth liquid delivery. The only difference between the construction of the test body D and the construction of the test body C lay in the fact that the particle strands or ribbons in the particle layers 32, 33 applied to the body D overlapped one another horizontally to an extent referenced a in the Figure, whereas the particle strands in the particle layers 30, 31 applied to the body C were mutually spaced horizontally and it is probably this structural difference that caused the liquid-receiving properties of the test body D to be far better than the liquid-receiving properties of the test body C. The test bodies C and D were manufactured by the method described above with reference to FIG. 2 and it is apparent that the relative positioning of the slots in the particle layers of these bodies locally influenced the compression of the layers of cellulose fluff present in the bodies such as to obtain a varied compression profile, this variation depending on whether, as seen vertically, the body included local parts of both the particle layers 30, 31 and 32, 33 respectively, an opening 34, 35 and a particle layer in addition to the cellulose fluff layers 26, 27, instead of containing solely two openings 35. It is therefore reasonable to assume that the large difference between the liquid-receiving properties of the bodies C and D was the result of the difference in the mutually relative position of the openings 34 and 35 in the two particle layers 30, 31 and 32, 33 respectively, and therewith associated differences in the compression pattern of the cellulose fluff layers 26, 27 of the test bodies C and D.

Figure 7:
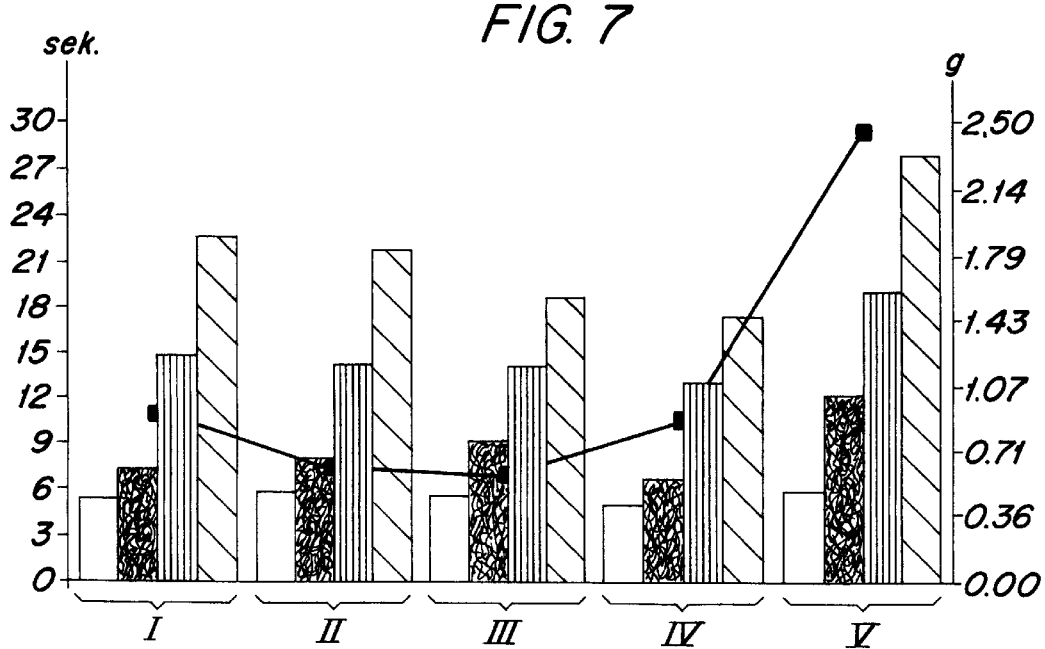
FIG. 7 is a bar chart illustrating the liquid-receiving time for the test bodies in FIG. 6 on four successive liquid discharge occasions and rewetting after the third liquid discharge occasion.
Figure 6:
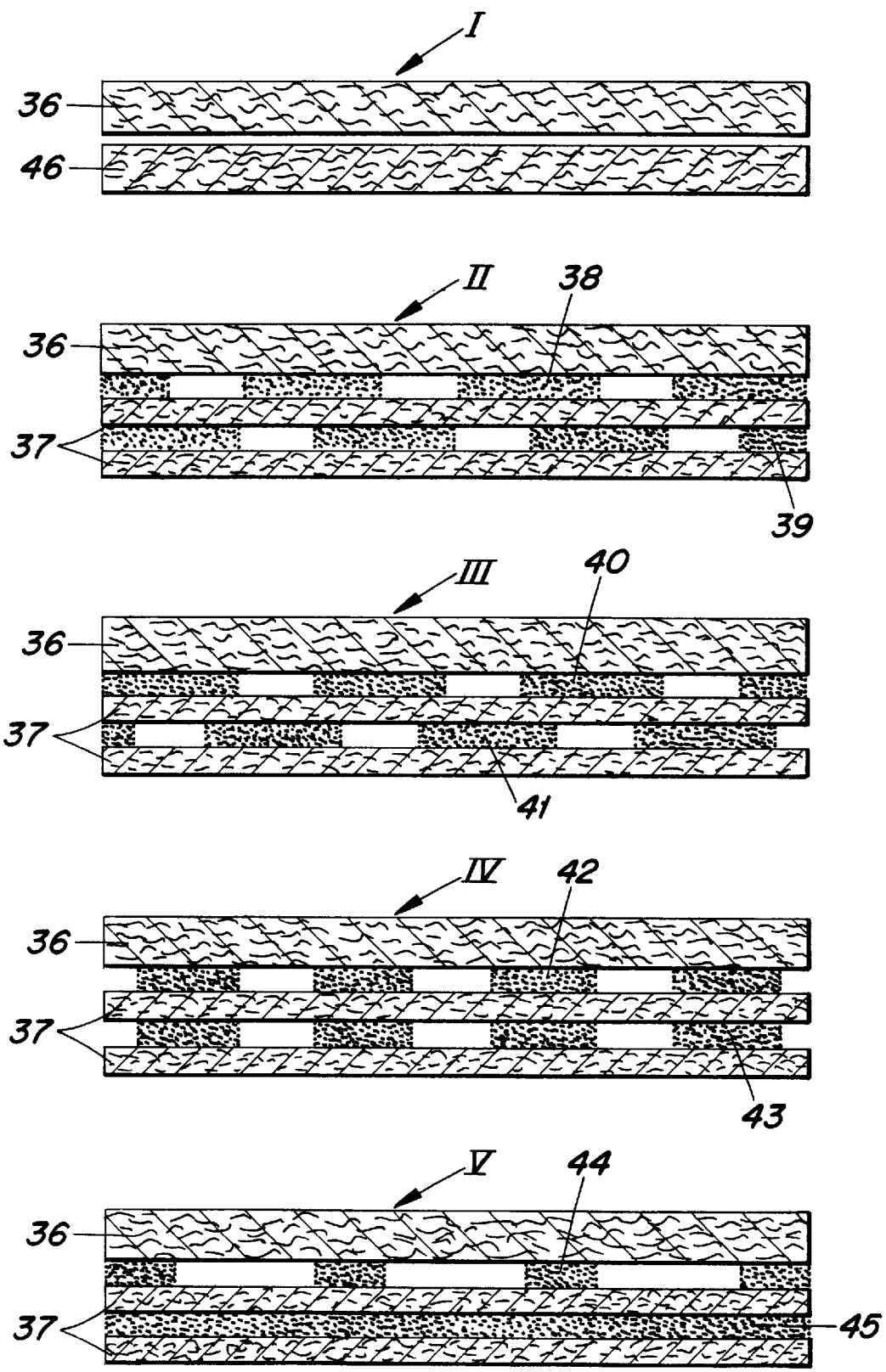
FIG. 6 illustrates schematically cross-sectional views of five further test bodies.

Four different test bodies II-V constructed in accordance with the invention were tested in the same manner as the test bodies C and D and compared with a test body I. The result of this comparison test is shown in FIG. 7 in the form of a stack chart which illustrates the liquid admission time in seconds and quadrates the recorded weights in grams of liquid absorbed in the rewetting test, in the same way as the test results obtained with the test bodies A–D illustrated in FIG. 5. The test procedures applied were the same as those described above for testing the test bodies A–D.

Each of the four inventive test bodies II-V comprised a top layer 36 of chemithermomechanical cellulose fluff pulp in which particles of superabsorbent material were homogenously admixed. The superabsorbent material corresponded to 10 percent by weight. The surface weight of the top layers 36 were 275 g/m². Each test body II-V also included two layers 37 of chemical cellulose fluff pulp having a surface weight of 150 g/m² and carrying respective layers 38–45 of superabsorbent particles.

The layers 38, 39 of the test body II comprised longitudinally extending strands of superabsorbent particles having a surface weight of 157 g/m² and separated by open slots. The pattern of strands and slots was similar in the two layers 38, 39, although the patterns in respective layers were displaced transversely in relation to one another, so that both particle strands and slots overlapped one another. The open area in the particle layers 38, 39 was 30%.

The layers 40, 41 of the test body III comprised longitudinally extending strands of superabsorbent particles having a surface weight of 160 g/m² and mutually separated by open slots. The test body III differed from the test body II by virtue of the fact that its strands and slots were displaced transversely in relation to one another, so that the particle strands overlapped one another but not the slots. Thus, the particle strands in one layer of the sample body III completely overlapped the slots in the other layer. The open areas in the particle layers 40, 41 were 30 and 35% respectively.

The layers 42, 43 of superabsorbent particles in the test body IV comprised longitudinally particle strands having a surface weight of 183 g/m² and being mutually spaced by open slots disposed, as earlier, in a uniform pattern. In this case, the patterns are not displaced transversely in relation to one another and the particle strands and slots completely overlap each other. The two layers had an open area of 40%.

The uppermost layer 44 of the test body V comprised particle strands having a surface weight of 157 g/m² and being separated by open slots. The uppermost layer 44 had an open area of 60%. The bottom particle layer 45 comprised an unbroken layer which had a surface weight of 157 g/m².

The test bodies II-V were compared with a test body I which comprised a similar top layer 36 to the test bodies II-V and a bottom layer 46. The bottom layer 46 was comprised of a chemical cellulose fluff pulp having a surface weight of 300 g/m² and with which there were admixed homogeneously 6.16 g of superabsorbent particle material. The bottom layer had a total surface weight of 220 g/m².

All of the test bodies I-V measured 100×280 mm and were constructed from mutually the same material.

The test bodies I-V were tested in the manner described above with reference to test bodies A–D and the result of the test is shown in FIG. 7, in which the mutually sequential stacks illustrate the respective admission times of the different test bodies for successive liquid deliveries. It will be seen from this Figure that the liquid-receiving properties of the test bodies II-IV corresponded essentially with the liquid-receiving properties of the test body I, which was comprised of two layers of cellulose fluff pulp and an admixture of superabsorbent particles. The properties of the test bodies III and IV were found to be better than the properties of the test body I on the fourth liquid delivery. Rewetting tendencies were far less pronounced in the case of test bodies II and III than in the case of test body I, whereas rewetting in the case of test body IV corresponded essentially to the rewetting tendency of test body I. The liquid-receiving and rewetting properties of test body V were poorer than the properties of test body I.

These tests thus show that absorbent bodies which include particle layers in which openings are provided and in which the openings in different layers are displaced in relation to one another have good liquid-receiving and rewetting properties.

Figure 9:
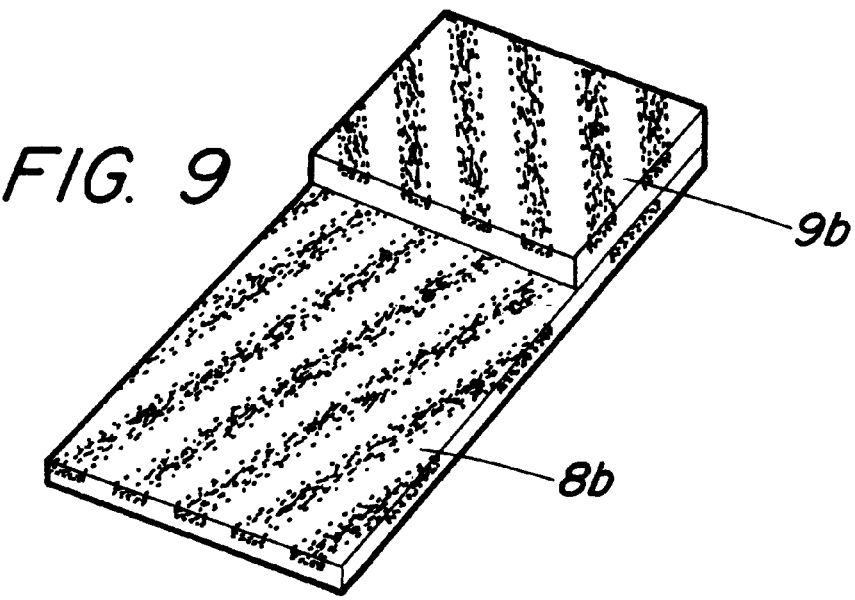
FIG. 9 illustrates schematically a cross-sectional view of a further embodiment of the present invention.
Figure 8:
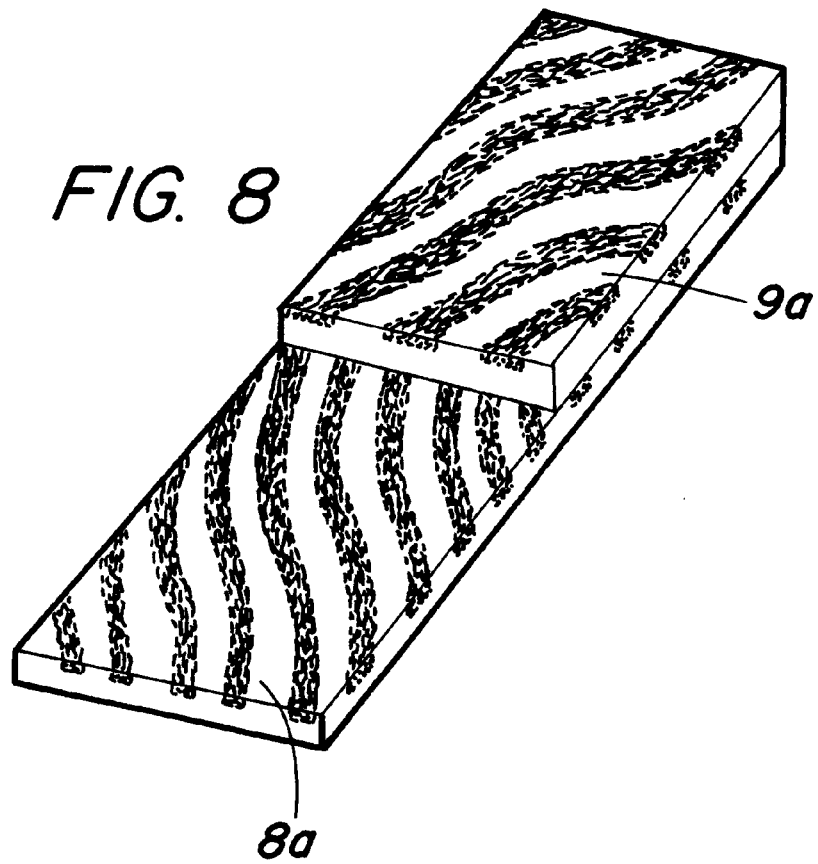
FIG. 8 illustrates schematically a cross-sectional view of a further embodiment of the present invention.

It will be understood that the illustrated and described embodiment can be modified in several ways. For instance, the pattern of openings in the particle layers may be different to those shown. For instance, instead of parallel slots, the slots may be curved as shown by reference numeral 8a, 9a in FIG. 8, angled as shown by reference numeral 8b, 9b in FIG. 9, circular, or in the form of holes having a circular or some other shape, etc. Furthermore, the layers of absorbent material may be pre-compressed and the absorbent bodies may have shapes other than rectangular. The invention also includes absorbent body constructions which include a particle layer that has only one single opening, although such constructions are not preferred. Embodiments which include more than two particle layers are also conceivable, of course. Absorbent materials other than those recited above may also be used, although it is preferred to produce the bottom layer or layers from chemical cellulose fluff pulp because of its good liquid-dispersion properties. The devices used in the manufacturing plant machinery may also be configured differently to that described. For instance, transport means for pre-compressed fibre bodies may be used instead of mat-forming wheels, and the number of devices included may be adapted to produce bodies which contain more or fewer layers than the arrangement illustrated in FIG. 2. The superabsorbent particles may also be deposited in ways other than that described. The invention is therefore restricted solely by the content of the following claims.

What is claimed is:

1. An absorbent body for an absorbent article, said absorbent body comprising:

at least two layers of absorbent material, a layer of superabsorbent particles laid upon each of said at least two layers, said particle layers including patterns of superabsorbent particles and through-penetrating openings between said superabsorbent particles, said through-penetrating openings being defined where there are substantially no superabsorbent particles, one of said layers of absorbent material being secured above another of said layers of absorbent material such that said through-penetrating openings of said particle layer of said one layer of absorbent material are horizontally displaced in relation to said through-penetrating openings of said particle layer of said another layer of absorbent material such that said openings defined where there are substantially no superabsorbent particles in said one layer are not vertically aligned with said openings defined where there are substantially no superabsorbent particles in said another layer.

2. An absorbent body according to claim 1, wherein the absorbent material is comprised of a fibre structure; and the particles in the particle layers are completely or partially enclosed in the fibre structure.

3. An absorbent body according to claim 2, wherein the layers of absorbent material comprise compressed cellulose fluff pulp; and the through-penetrating openings in the particle layers are filled with cellulose fluff pulp which has been compressed to a lesser extent than said compressed cellulose fluff pulp of said absorbent material layers.

4. An absorbent body according to claim 3, wherein the compressed cellulose fluff pulp of said absorbent material layers comprise a cellulose fluff pulp having liquid-dispersion ability.

5. An absorbent body according to claim 4, wherein the compressed cellulose fluff pulp of said absorbent material layers comprise chemical cellulose fluff pulp.

6. An absorbent body according to claim 1, wherein the pattern of openings in each particle layer comprises mutually spaced slots which extend parallel with one another in the longitudinal direction of the absorbent body along at least a substantial part of its length.

7. An absorbent body according to claim 6, wherein the slots in the particle layers are angled with respect to the longitudinal axis of the absorbent body.

8. An absorbent body according to claim 7, wherein the slots in mutually adjacent particle layers extend at different angles to the longitudinal axis of the absorbent body.

9. An absorbent body according to claim 6, wherein the slots in the particle layers have a curved shape.

10. An absorbent body according to claim 9, wherein the curved shaped of the slots in the particle layers is sinusoidal.

11. An absorbent body according to claim 6, wherein mutually adjacent slots or rows of holes in each particle layer slope at different angles to the longitudinal axis of the absorbent body.

12. An absorbent body according to claim 1, wherein a layer of fibre structure having a liquid-receiving ability is arranged on top of an uppermost particle layer, which, in the case of an absorbent article that includes the absorbent body, will lie proximal to the wearer's body when the article is worn.

13. An absorbent body according to claim 12, wherein particles of superabsorbent material are admixed in the layer of liquid-receiving ability.

14. An absorbent body according to claim 12, wherein the fibre structure comprises chemithermomechanical fluff pulp having a high liquid-receiving ability.

15. An absorbent body according to claim 12, wherein the fibre structure comprises chemically stiffened cellulose fibres having a high liquid-receiving ability.

16. An absorbent body according to claim 12, wherein the fibre structure comprises synthetic wadding having a high liquid-receiving ability.

17. An absorbent body according to claim 1, wherein the pattern of openings in each particle layer is comprised of longitudinally extending rows of holes.

18. An absorbent body according to claim 17, wherein the holes in the particle layers are circular.

19. An absorbent body according to claim 17, wherein the holes in the particle layers are rectangular.

20. An absorbent body according to claim 17, wherein the holes in the particle layers have a ring shape.

21. An absorbent body according to claim 1, wherein one of said particle layers is adjacent to another of said particle layers, particles in the one of said particle layers present between the openings fully overlap the openings in said adjacent particle layers.

22. An absorbent body according to claim 1, wherein one of said particle layers is subjacent to another of said particle layers.

23. An absorbent body according to claim 1, wherein said particle layers are horizontally displaced in a direction defined through a thickness of the absorbent body.

24. An apparatus for manufacturing absorbent bodies for absorbent articles such as diapers, incontinence guards or sanitary napkins, the apparatus comprising:

means for passing a first fibre body past particle applicator means, means for delivering particles in a first predefined pattern containing particles and through-penetrating openings onto said first fibre body, said through-penetrating openings being defined by a general lack of particles, means for placing a second fibre body on top of the first fibre body after having applied the layer of particles to said first fibre body, means for applying to the second fibre body a layer of particles in a second predefined pattern containing particles and through-penetrating openings, said through-penetrating openings being defined by a general lack of particles, said second predefined pattern of particles and through-openings being displaced in relation to the first predefined pattern of particles and through-openings applied to the first fibre body such that the through-openings of the second fibre body are displaced and therefore not vertically aligned in relation to the through-openings of the first fibre body disposed therebelow, and means for compressing the thus obtained composite absorbent body.

25. An apparatus according to claim 24, wherein the means for applying particles to the first and the second fibre body each includes a particle dispenser, a belt which moves over the fibre body concerned, the belt including a hole pattern corresponding to one of the first and second given particle patterns, wherein the particle dispenser is intended to dispense particles continuously in a uniform and broad stream whose width is equal to or slightly greater than the width of the hole pattern on the belt, and further includes means for removing particles caught by the belt.

26. An absorbent article, comprising:

an absorbent body having at least two layers of absorbent material, upon each of which a layer of superabsorbent particles has been laid, said particle layers including patterns of through-penetrating openings and one of said particle layers being horizontally displaced in relation to another of said particle layers, wherein said absorbent body is enclosed between a liquid-permeable casing layer and a liquid-impermeable casing layer.

* * * * *